United States Patent
Bernard et al.

(10) Patent No.: US 6,287,542 B1
(45) Date of Patent: Sep. 11, 2001

(54) ENCAPSULATION

(75) Inventors: Laurence Marie Bernard; Jonathan Edward Creeth; William John Stead, all of Bebington, Wirral (GB)

(73) Assignee: ilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/503,920

(22) Filed: Feb. 14, 2000

(30) Foreign Application Priority Data

Feb. 15, 1999 (EP) .................................................. 99301095

(51) Int. Cl.$^7$ ...................................................... A61R 7/16
(52) U.S. Cl. ............................................. 424/49; 424/417
(58) Field of Search ................................. 424/40, 52, 54, 424/417–420; 264/4.1, 4.3; 428/402.2

(56) References Cited

U.S. PATENT DOCUMENTS

| | | | |
|---|---|---|---|
| 4,224,346 | * 9/1980 | Sprecker et al. | 426/3 |
| 4,797,392 | * 1/1989 | Chernomorsky | 514/185 |
| 5,077,053 | * 12/1991 | Kuncewitch et al. | 424/441 |
| 5,700,449 | * 12/1997 | Katayama et al. | 424/49 |

FOREIGN PATENT DOCUMENTS

| | | |
|---|---|---|
| 0 711 544 | 5/1996 | (EP) . |
| 0 711 544 A2 * | 5/1996 | (EP) . |
| 1381444 | 1/1975 | (GB) . |
| 55161863 | 12/1980 | (JP) . |
| 62125369 | 6/1987 | (JP) . |
| 2034555 | 5/1995 | (RU) . |
| 955929 | 9/1982 | (SU) . |

OTHER PUBLICATIONS

European Search Report Jul. 1999.
Chemical Abstract 111:160056 1989.

* cited by examiner

*Primary Examiner*—Ralph Gitomer
(74) *Attorney, Agent, or Firm*—Milton L. Honig

(57) ABSTRACT

The present invention relates to a process for treating a mixture of a liquid oil and a copper chlorophyll extract with a mixture of at least 90% by weight of a $C_2$–$C_4$ alcohol, and water at a certain concentration. The thus treated mixture is then suitable for making micro capsules with a green colorer liquid core material comprising said mixture by means of complex coaceration. These microcapsules can be included in oral care products to import a speckled appearance thereto. The liquid oil is typically sunflower oil or paraffin oil, and the $C_2$–$C_4$ alcohol is typically ethanol or isopropanol.

13 Claims, No Drawings

ENCAPSULATION

BACKGROUND OF THE INVENTION

1. Field of the Invention

The present invention relates to a process for treating a mixture of an oil and a copper chlorophyll extract with a solvent to render such mixture e.g. suitable for making microcapsules which contain a liquid core material comprising a mixture of oil and copper chlorophyll, said microcapsules e.g. being particularly suitable for use in oral care products.

2. The Related Art

It has already been previously suggested in the art to include microcapsules which contain an oily core and colouring agent in oral care products, primarily to impart a "speckled" or "spotty" colouring effect thereto. Thus, for example, GB-A-1,381,444 (Blendax) describes microcapsules having a transparent shell material encapsulating a solution or suspension of colouring matter in a physiologically inert solvent such as paraffin oil. These microcapsules can be included in toothpastes to impart a speckled colouring effect thereto. The colouring materials are colouring agents or pigments such as various C-reds, C-blues, and C-greens, the latter including C-green 8 which is a mixture of a copper chlorophyll complex and a copper chlorophyllin complex. These microcapsules can be made by well-known encapsulation processes, such as coacervation, using e.g. gelatine as the encapsulating material.

However, we have found that it is not possible to obtain acceptable microcapsules according to this prior proposal when using copper chlorophyll as the colouring agent. Dissolving copper chlorophyll in the paraffin oil gave a precipitate of small, blackish particles when added to water, thus making the mixture unsuitable for obtaining acceptable microcapsules by means of coacervation.

In EP-A-0,711,544 (Kao) microcapsules for use in dentifrice compositions are described, which contain agar as the coat-forming material, and core material which may consist of a great variety of dentifrice ingredients and vehicles therefor. Among these dentifrice ingredients copper chlorophyll is also mentioned, and among the vehicles natural fats and oils as well as minerals oils are mentioned. While various production methods, including coacervation, are mentioned, a double nozzle dropping method is preferred to make the microcapsules.

In some of the working examples, microcapsules are described which contain as core material a medium chain triglyceride and sodium copper chlorophyllin.

However, sodium copper chlorophyllin is water-soluble, and we have found that it is not possible to obtain acceptable microcapsules which contain a core of an oil and sodium copper chlorophyllin by means of coacervation according to this prior proposal. A green sludge was formed at the oil/water interface during the emulsification step, which prevented capsule wall formation. The same was found when using copper chlorophyll instead of the sodium copper chlorophyllin.

Chlorophyll extracts are usually obtained by suitable extraction of plant leaves such as alfalfa, grass, nettles.

The extracts normally contain chlorophyll a and b, as well as a number of other ingredients such a pigments, carbohydrates, waxes, fats, oils, salts, proteins and xanthophyll.

Copper chlorophyll extracts are usually obtained by replacing in the chlorophyll extract the magnesium ion at the centre of the porphyrin ring by copper.

Commercial grades of copper chlorophyll extract (INCI name: Chlorophyllin-Copper Complex or CI 75810; EINECS No. 234-242-5) are usually mixtures of copper chlorophyll extract and a vegetable oil, containing up to 15% copper chlorophyll.

SUMMARY OF THE INVENTION

We have now found, quite unexpectedly, that by treating a mixture of a copper chlorophyll extract and an oil with a mixture of at least 90% by weight of a $C_2$–$C_4$ monohydric alcohol, which is miscible with water in all proportions, the balance of the mixture being water, and subsequently separating the resulting alcoholic and oily layers, an oil- and copper chlorophyll-containing mixture is obtained which is quite suitable for making quite acceptable microcapsules containing a liquid core material comprising said mixture by means of coacervation methods. These microcapsules contain a green liquid core, and a translucent or transparent, outer shell, thus providing for a speckled appearance to the oral care products in which they may be included, without causing the presence of unsightly burst capsule skins upon use of such oral care products. Preferably, a mixture of at least 96% by weight of a $C_2$–$C_4$ monohydric alcohol which is miscible with water in all proportions, the balance being water, is used. Suitable examples of the $C_2$–$C_4$ monohydric alcohols are ethanol, propanol, isopropanol, butanol, isobutanol, tertiary butanol, and mixtures thereof. Preferred are ethanol and isopropanol, and particularly preferred is ethanol. We have found that optimum results are obtained, when using 97.5% absolute ethanol/2.5% water; up to 10% copper chlorophyll extract in the oil can thereby successfully treated.

The aforementioned commercial grades of copper chlorophyll are suitable starting materials for the process of the present invention. Naturally, it is also possible to mix a required amount of copper chlorophyll, obtained from other sources, with an oil to obtain the required starting material.

DETAILED DESCRIPTION OF THE INVENTION

Although it is possible to first treat the commercial grades of copper chlorophyll extract, containing an oil, with the alcohol/water mixture and subsequently recovering the oil- and copper chlorophyll-containing oily layer, and mixing said layer with an oil, it is preferred to first admix such commercial grades with an appropriate oil, and then treat said admixture with the process according to the present invention.

Thus, typically, the copper chlorophyll/oil mixture is mixed with the alcohol/water mixture in a ratio of 2:1 to 1:4 (expressed as parts of the copper chlorophyll/oil mixture to parts of the alcohol/water mixture), preferably 1 part of the copper chlorophyll/oil mixture to 2 parts of the alcohol/water mixture, preferably under vigorous agitation. The resulting mixture is then allowed to stand until the phases have separated, usually for at least 12 hours. The resulting green oil-phase is then separated from the alcohol-containing phase, mixed again with the alcohol/water mixture in the same ratio, and allowed to stand until the phases have separated, usually for at least 6 hours. The resulting green oil-phase is then washed with water to remove traces of alcohol.

The thus-obtained green oil is subsequently admixed with a liquid oil to form the liquid core material for the microcapsules to be formed by a coacervation process. The liquid oil can be selected from well-known liquid vegetable or animal edible oils, such as soybean oil, rapeseed oil, cottonseed oil, coconut oil, palm oil, palm kernel oil, sunflower oil, groundnut oil, safflower oil, fish oil, whale oil and the like, as well as synthetic analogues thereof, as well as fatty acid mono- and/or -diglycerides. The liquid oil can also be an inert, physiologically acceptable mineral oil such as paraffin oil. The liquid oil should be liquid or liquefiable at the encapsulating temperature or below, usually at 60° C. or below, and preferably at 25° C. or below. Mixtures of the various oils can also be used. A particularly preferred oil is sunflower oil. The resulting mixture should not have too high or too low a viscosity, as otherwise the coacervation process would not yield acceptable microcapsules. The viscosity should in general not be higher than 5 Pa.s and not lower than 0.004 Pa.s. If required, the viscosity can be adjusted by inclusion of a small amount of a thickening agent, e.g. up to 5% of beeswax or beeswax ester or a thickening silica.

The oil/copper chlorophyll mixture and the liquid core oil are usually admixed in a weight ratio of 1:5 to 1:1000, preferably 1:10 to 1:50 to form the liquid core material for the microcapsules.

The liquid core material may also contain small amounts of gum health agents such as antimicrobial agents like Triclosan; vitamins, enzymes, keratin; furthermore flavouring oils, preservatives like sodium and potassium benzoate, antioxidants such as butylated hydroxytoluene (BHT), butylated hydroxyanisole (BHA), propyl-, octyl-, dodecyl gallate, tertiary butylhydroxyquinone (TBHQ), ascorbylpalmitate, rosemary oil; oil crystallisation inhibitors such as lecithin or sorbitol fatty acid esters may also be included.

The microcapsules are made by means of well-known coacervation processes. Coacervation is the formation of a liquid aggregate in the form of viscous droplets by salting out of a hydrophilic sol. Such droplets, or coacervates, are formed most readily when two hydrophilic sols carrying opposite charges, e.g. gelatine and gum arabic are mixed in suitable amounts.

According to the present invention, preferably a mixture of gelatine and gum arabic, preferably cross-linked, e.g. with glutaraldehyde, is used to form the outer shell of the microcapsules. Preferably, a complex coacervation process is used. The liquid core material is emulsified with a warm (40–60° C.) aqueous gelatine solution. The gum arabic and water are added to this emulsion, and the pH of the aqueous phase adjusted to 4.0–4.5. The aqueous phase preferably contains a preservative such as potassium sorbate. This causes the formation of a complex coacervate of gelatine, gum arabic and water, which adsorbs on the surface of the liquid core material, forming a film around the dispersed core material thereby forming microcapsules. Subsequently the system is cooled, often below 10° C., to solidify the coacervate shell. Glutaraldehyde is then added to cross-link the shell.

Thereafter, the aqueous slurry of the microcapsules can be used as such, or dried to a free-flowing powder. The microcapsule size thus obtainable typically ranges from 200–2000 micrometers. The microcapsules may have a transparent or translucent outer shell, and a green colorer liquid or low melting point solid core, thus making them readily visible in an oral care product.

The microcapsules are usually included in the oral care product in an amount of from 0.1–5% by weight, preferably 0.5–4%, usually 1–3% by weight.

The oral care products in which the microcapsules can be incorporated can be of any well-known type, such as pastes and gels. The gel type is preferred, in order to make the microcapsules more readily visible, giving an attractive aesthetic speckled or spotty appearance to the gel-type oral care product.

The oral care compositions may comprise optional, conventional ingredients such as pharmaceutically acceptable carriers like starch, sucrose, water or water/alcohol systems etc.. Small amounts of surfactants may also be included, such as anionic, nonionic, cationic and zwitterionic or amphoteric surfactants. They may comprise particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight. Water-soluble mildly abrasive salts like sodium bicarbonate and sodium carbonate may additionally be included.

Furthermore, they may comprise humectants such as glycerol, sorbitol, propyleneglycol, xylitol, lactitol and so on.

Binders and thickeners such as sodium carboxymethylcellulose, xanthan gum, gum arabic etc. may also be included, as well as synthetic polymers such as polyacrylates and carboxyvinyl polymers such as Carbopol®.

Flavours such as peppermint and spearmint oils may also be included, as well as preservatives such as sodium benzoate, opacifying agents, colouring agents, pH-adjusting agents, buffering agents such as potassium citrate and potassium tartrate, sweetening agents and so on.

Anti-bacterial agents may also be included such as Triclosan, chlorhexidine, copper-, zinc- and stannous salts such as zinc citrate, sodium zinc citrate and stannous pyrophosphate, sanguinarine extract, metronidazole. Further examples of anti-bacterial agents are quaternary ammonium compounds such as cetylpyridinium chloride; bis-guanides such as chlorhexidine digluconate, hexetidine, octenidine, alexidine; halogenated bisphenolic compounds such as 2,2' methylenebis-(4-chloro-6-bromophenol).

Polymeric compounds which can enhance the delivery of active ingredients such as anti-bacterial agents can also be included. Examples of such polymers are copolymers of polyvinylmethylether with maleic anhydride and other similar delivery enhancing polymers, e.g. those described in DE-A-3,942,643 (Colgate)

Furthermore anti-inflammatory agents such as ibuprofen, flurbiprofen, aspirin, indomethacin etc. may also be included.

Anti-caries agents such as sodium- and stannous fluoride, aminefluorides, sodium monofluorophosphate, casein; plaque buffers such as urea, calcium lactate, calcium glycerophosphate, strontium polyacrylates may also be included. Other optional ingredients include vitamins such as Vitamin C, and plant extracts. Additional desensitising agents such as glycerol monooleate, potassium citrate, potassium chloride, potassium tartrate, potassium bicarbonate, potassium oxalate, potassium nitrate as well as strontium salts may also be included.

Buffers and salts to buffer the pH and ionic strength of the compositions may also be included.

Furthermore, the oral compositions may comprise anti-calculus agents such as alkalimetal pyrophosphates, hypophosphite-containing polymers, organic phosphonates, phosphocitrates etc.

In addition, the compositions may comprise functional biomolecules such as bacteriocins, antibodies, enzymes and so on.

Other optional ingredients that may be included are e.g. bleaching agents such as peroxy compounds e.g. potassium peroxydiphosphate, effervescing systems such as sodium bicarbonate/citric acid systems, colour change systems, and so on.

The toothpastes may also be formulated into systems for use in dual-compartment type dispensers.

The present invention is further illustrated by way of Example. In all the Examples the starting material was copper chlorophyll extract as supplied by the supplier (a 13% solution of copper chlorophyll in a vegetable oil). This was diluted subsequently by a factor 10 with sunflower oil to give a mixture of vegetable and sunflower oil with 1.3% copper chlorophyll extract. This mixture is hereafter referred to as "the Mixture".

EXAMPLE 1

The Mixture was vigorously mixed with 97.5% ethanol/ 2.5% deionized water (1 part oil mixture to 2 parts of ethanol/water) in a separating funnel for about 1 minute, opening the tap periodically to allow ethanol vapour to escape. The resulting mixture was allowed to stand for 6 hours. Thereafter, the green oil phase was run off from the separating funnel, and was mixed again with the same proportion of the ethanol/water mixture and allowed to stand for 3 hours. The resulting green oil phase was run off and washed with water to remove remaining traces of ethanol. The green oil, thus obtained, was subsequently mixed with sunflower oil in an amount such, that the final mixture contained 0.5% by weight of the copper chlorophyll of the original concentration of the starting material as supplied. This final mixture was used as the liquid core material for making microcapsules containing same according to the following complex coacervation process. The liquid core material was dispersed and emulsified in a warm (50° C.) aqueous gelatine solution. Gum arabic and water were added to this emulsion, the pH of the aqueous phase being adjusted with acetic acid to 4.8. The resulting mixture was slowly cooled to room temperature, and subsequently glutaraldehyde was added. An aqueous slurry of 60% microcapsules in water was obtained. The amounts of gelatine and gum arabic used were such, that the shell of the microcapsules consisted of a 50:50 mixture of gelatine and gum arabic (1.5% of each in the product), cross-linked with glutaraldehyde. 0.5% Potassium sorbate was added as preservative during the complex coacervation process. The microcapsules had an average diameter of 900 micrometers, had a transparent outer shell and a green liquid core.

EXAMPLE 2

The Mixture was shaken with 96% ethanol/4% deionized water in a separating funnel for about 1 minute, opening the tap periodically to allow ethanol vapour to escape. The mixture was allowed to stand for 6 hours. The resulting green oil phase was run off from the separating funnel, precipitating material remaining in the ethanolic layer. This oily layer formed a clean interface with water when it was emulsified with water, and was found to be suitable for use in a complex coacervation process to form microcapsules. The oil phase had, however, become slightly less viscous than originally, and smelt somewhat of ethanol, making the microcapsules somewhat less attractive for use in an oral care product.

EXAMPLE 3

Repeating Example 1, but mixing the green oil phase, obtained after the ethanol treatments with a white mineral oil in such an amount, that the final liquid core material contained 5% sunflower oil, resulted in similar microcapsules as in Example 1.

Repeating this Example, but using a semi-soft triglyceride, or sunflower oil which had been thickened with 2.5% beeswax or 2.5% beeswax ester, instead of the mineral oil gave microcapsules, which were somewhat opaque and less visually appealing than those, obtained in Example 1 or with mineral oil according to this Example 3.

EXAMPLE 4

The Mixture was treated in a similar manner as in Example 3, but with various ethanol/water concentrations. The finally obtained ethanolic aqueous phase was assessed as to its clarity by means of spectrophotometic analysis, using a wave-length of 540 nm. The following results were obtained:

| Ethanol/water concentration (in %) | Absorbance at $\lambda$ = 540 nm |
|---|---|
| Reference (non treated Mixture + mineral oil) | 0.2245 |
| 85/15 | 0.1380 |
| 90/10 | 0.0995 |
| 92.5/7.5 | 0.0935 |
| 95/5 | 0.0700 |
| 97.5/2.5 | 0.0595 |
| 100/0 | 0.0810 |

These results showed, that the ethanolic aqueous phase, obtained with 97.5/2.5 ethanol/water was the most clear.

EXAMPLE 5

To a conventional gel-type toothpaste, 1% of the microcapsules according to Example 1 were added. The resulting toothpaste had an attractive, green speckled appearance. Consumer studies indicated a satisfactory foam level to be obtained with this paste.

What is claimed is:

1. A process for treating a mixture of a liquid oil and a copper chlorophyll extract, to render said mixture suitable for making microcapsules with a liquid core material comprising said mixture, characterised in that said mixture is admixed with a mixture of at least 90% by weight of a $C_2$–$C_4$ monohydric alcohol, which is miscible with water in all proportions, the balance of the mixture being water, allowing the resulting mixture to form an alcoholic and an oily layer, and separating the oily layer from the alcoholic layer.

2. A process according to claim 1, characterised in that the separated oily layer is again treated with a mixture of at least 90% by weight of a $C_2$–$C_4$ monohydric alcohol, which is miscible with water in all proportions, the balance of the mixture being water, again allowing the resulting mixture to form an alcoholic and an oily layer, and separating the oily layer from the alcoholic layer.

3. A process according to claim 1, characterised in that the mixture of liquid oil and copper chlorophyll extract is admixed with a mixture of at least 96% by weight of a $C_2$–$C_4$ monohydric alcohol, which is miscible with water in all proportions, the balance of the alcohol mixture being water.

4. A process according to claim 1, characterised in that the alcohol is ethanol or isopropanol.

5. A process according to claim 4, characterised in that the mixture of alcohol and water is 97.5% ethanol/2.5% water.

6. A process according to claim 1 further comprising forming with shell-forming agents an outer shell around the liquid core material by means of complex coacervation.

7. A process according to claim 6, characterised in that the liquid oil is sunflower oil or paraffin oil.

8. A process according to claim 6, characterised in that the complex coacervation is carried out with a mixture of gelatine and gum arabic as the shell-forming agents of the microcapsules.

9. A process according to claim 8, characterised in that the microcapsules are treated with glutaraldehyde.

10. A process according to claim 6, characterised in that the liquid core material further comprises gum health benefit agents selected from the group consisting essentially of antimicrobial agents, vitamins, enzymes, keratin, flavoring oils, preservatives, antioxidants and oil crystallization inhibitors.

11. A process comprising:
   (i) providing a liquid oil colored green by an effective coloring amount of a copper chlorophyll extract;
   (ii) treating the colored liquid oil with a mixture miscible with water in all proportions comprising at least 90% by weight of a $C_2$–$C_4$ monohydric alcohol and water forming the balance of the mixture;
   (iii) separating the colored liquid oil from the mixture of alcohol and water; and
   (iv) forming the separated colored liquid oil into a core and surrounding the core by an outer shell material thereby creating microcapsules.

12. A process according to claim 11, wherein the colored liquid oil and mixture miscible with water are present in a respective ratio of 2:1 to 1:4.

13. A process according to claim 11 wherein coacervation is utilized to surround the core by an outer shell material.

* * * * *

UNITED STATES PATENT AND TRADEMARK OFFICE
CERTIFICATE OF CORRECTION

PATENT NO. : 6,287,542 B1
DATED : September 11, 2001
INVENTOR(S) : Bernard et al.

It is certified that error appears in the above-identified patent and that said Letters Patent is hereby corrected as shown below:

<u>Title page,</u>
Please change the Assignee from "ilever Home & Personal Care USA, a division of Conopco, Inc." to read -- Unilever Home & Personal Care USA, Division of Conopco, Inc. --

Signed and Sealed this

Second Day of July, 2002

*Attest:*

JAMES E. ROGAN
*Attesting Officer*  *Director of the United States Patent and Trademark Office*